United States Patent
Kanaki et al.

(10) Patent No.: US 10,092,687 B2
(45) Date of Patent: Oct. 9, 2018

(54) BLOOD FILTER AND METHOD FOR MANUFACTURING THE SAME

(71) Applicant: NISSAN CHEMICAL INDUSTRIES, LTD., Chiyoda-ku, Tokyo (JP)

(72) Inventors: Tatsuro Kanaki, Shiraoka (JP); Takahiro Kishioka, Toyama (JP); Taito Nishino, Shiraoka (JP); Yoshiomi Hiroi, Toyama (JP); Ayako Otani, Shiraoka (JP); Tomoyuki Ozawa, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 114 days.

(21) Appl. No.: 14/896,632

(22) PCT Filed: Jun. 9, 2014

(86) PCT No.: PCT/JP2014/065249
§ 371 (c)(1),
(2) Date: Dec. 7, 2015

(87) PCT Pub. No.: WO2014/196651
PCT Pub. Date: Dec. 11, 2014

(65) Prior Publication Data
US 2016/0129176 A1  May 12, 2016

(30) Foreign Application Priority Data

Jun. 7, 2013  (JP) .................. 2013-121111
Oct. 3, 2013  (JP) .................. 2013-208514

(51) Int. Cl.
*A61M 1/36* (2006.01)
*B01D 39/16* (2006.01)
(Continued)

(52) U.S. Cl.
CPC ....... *A61M 1/3633* (2013.01); *B01D 39/1623* (2013.01); *B01D 71/26* (2013.01); *B01D 71/82* (2013.01); *A61M 2202/0439* (2013.01)

(58) Field of Classification Search
None
See application file for complete search history.

(56) References Cited

U.S. PATENT DOCUMENTS 5,643,561 A  7/1997  Katsuen et al.
5,658,561 A *  8/1997  Nakabayashi ...... A61L 33/0088
                                                          424/424
2012/0024779 A1  2/2012  Ochiai et al.

FOREIGN PATENT DOCUMENTS

EP  0561379 A1  9/1993
EP  0606646 A1  7/1994
(Continued)

OTHER PUBLICATIONS

European Patent Office, Extended European Search Report in European Patent Application No. 14808110.2 (dated Nov. 9, 2016).
(Continued)

*Primary Examiner* — Krishnan S Menon
(74) *Attorney, Agent, or Firm* — Leydig, Voit & Mayer, Ltd.

(57) ABSTRACT

This is to provide a blood filter comprising a porous element; and a copolymer which exists in at least a part of a surface of the porous element, and which contains a recurring unit containing an organic group of the following formula (a) and a recurring unit containing an organic group of the following formula (b),
wherein $U^{a1}$, $U^{a2}$, $U^{b1}$, $U^{b2}$ and $U^{b3}$, and $An^-$ are as defined in the present specification and the claims.

(Continued)

(a)

(b)

(a)

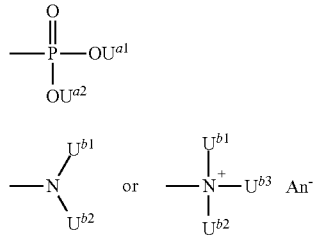

12 Claims, 2 Drawing Sheets

(51) Int. Cl.
*B01D 71/26* (2006.01)
*B01D 71/82* (2006.01)

(56) References Cited

FOREIGN PATENT DOCUMENTS

| JP | H06-247862 A | 9/1994 |
| JP | 2002-291875 A | 10/2002 |
| JP | 2007-063459 A | 3/2007 |
| JP | 2007-304016 A | 11/2007 |
| WO | WO 2010/113632 A1 | 10/2010 |

OTHER PUBLICATIONS

Japanese Patent Office, International Search Report in International Patent Application No. PCT/JP2014/065249 (dated Aug. 19, 2014).
Japanese Patent Office, Notification of Reasons for Refusal in Japanese Patent Application No. 2015-521513 (dated Jun. 26, 2018) English translation.

* cited by examiner (a)    (b)

BLOOD FILTER AND METHOD FOR MANUFACTURING THE SAME

CROSS-REFERENCE TO RELATED APPLICATIONS

This patent application is the U.S. national phase of International Patent Application No. PCT/JP2014/065249, filed Jun. 9, 2014, which claims the benefit of Japanese Patent Application No. 2013-208514, filed on Oct. 3, 2013, and Japanese Patent Application No. 2013-121111, filed on Jun. 7, 2013, which are incorporated by reference in their entireties herein.

TECHNICAL FIELD

The present invention relates to a blood filter and a method for manufacturing the same. In particular, the present invention is also useful as a leukocyte removing filter which can selectively remove leukocyte from whole blood and a method for manufacturing the same.

BACKGROUND ART

Blood products are pharmaceutical products generally comprising a human blood or a material obtained therefrom as effective components, and roughly classified into blood products for blood transfusion and fractionated plasma products. "The blood products for blood transfusion" are all of the human blood (whole blood) or preparations (component preparation) in which components such as red blood cell, platelet and plasma are separated from or adjusted to the human blood, and the component preparation has been mainly used at present. On the other hand, "the fractionated plasma products" are materials in which plasma proteins necessary for treatment are separated to each spices from human blood plasma and purified, and may be mentioned an albumin preparation, an immunoglobulin preparation and a blood coagulation factor preparation as main products.

The blood products for blood transfusion have been subjected to the treatment of removing leukocytes before preservation as a measure of safety. This has been done for the purpose of decreasing side effects such as a reaction of fever and infectious disease, caused by leukocytes. For the removal of the leukocytes before preservation, there are a mechanical removing method using a blood collecting apparatus and a filtering method using a leukocyte removing filter and, for example, it has been recommended to reduce a number of the leukocytes contained in one bag of the blood products for blood transfusion to $1 \times 10^6$ cells or less.

In particular, in the points of easiness in operation and a low cost, a filtering method using, as a filter material, a fibrous porous element such as nonwoven fabric or a nonfibrous porous element such as porous ceramic has widely been used. Also, to improve removing efficiency of leukocytes or recovery efficiency of platelets of these filter materials, various techniques to coat the surface of a filter material with a surface treatment agent have been reported.

As such a coating agent (a surface treatment agent), for example, a polymer having a nonionic hydrophilic group and a basic nitrogen-containing functional group, more specifically, a copolymer comprising 97 mol % of 2-hydroxyethyl(meth)acrylate and 3 mol % of N,N-dimethylaminoethyl(meth)acrylate has been reported (for example, see Patent Document 1). Similarly, a copolymer containing a monomer (A) having a hydrophilic functional group, a monomer (B) having a basic functional group and a monomer (C) having a reactive functional group as monomer components and constituted by predetermined molar ratios, more specifically, a copolymer containing 2-methoxyethyl acrylate (monomer (A)), N,N-dimethylaminoethyl methacrylate (monomer (B)) and 2-hydroxyethyl methacrylate (monomer (C)) as monomer components and constituted by predetermined molar ratios has been reported (for example, see Patent Document 2). The latter copolymer has been said that adhesion and activation of the platelets are suppressed by the monomers (A) and (B), the leukocytes are selectively adhered, further by the monomer (C), fixation of the surface treatment agent to the substrate is continued, and at the time of production and use, the surface treatment agent is never desorbed (eluted) from the substrate.

Contrary to the coating agent (the surface treatment agent) showing adhesion to the leukocyte as mentioned above, a substrate having a polymer material containing a cation and an anion at the side chain on the surface thereof has been known to have a function of preventing adhesion of biological substances (protein, cell, etc.) since the surface has been maintained to be electrically neutral due to the electrostatic balance. A coating material using these functions has been proposed and, in recent years, various reports have been made on the fixation or immobilization method to glass or a polymer substrate, etc. For example, a coating film obtained by subjecting a film formed by a coating solution containing a polymer having a phosphoric acid ester group to heat treatment at 200 to 450° C. has been reported to be excellent in durability while maintaining protein non-adhesion characteristics (for example, see Patent Document 3), and these are expected to be a coating material which suppresses adhesion of various biological substances in the medical instruments, equipments, etc.

PRIOR ART DOCUMENTS

Patent Documents

Patent Document 1: JP 2002-291875A
Patent Document 2: WO 2010/113632A
Patent Document 3: JP 2007-63459A

SUMMARY OF THE INVENTION

Problems to be Solved by the Invention

An object of the present invention is to provide a blood filter and a method for manufacturing the same, in particular, to a leukocyte removing filter which can selectively remove leukocytes from blood, and a method for manufacturing the same. An object of the present invention is more specifically to provide a leukocyte removing filter in which removal efficiency of the leukocytes and recovery efficiency of platelets have been improved, and a method for manufacturing the same.

In the conventional filtering method using a fibrous porous element such as nonwoven fabric or a nonfibrous porous element such as porous ceramics as a filter material, blood components were non-selectively adhered to a filter material, so that removal efficiency of the leukocytes or recovery efficiency of platelets was not sufficient. To improve these efficiencies, whereas a technique for coating a surface of a filter material with a coating agent which shows adhesion to the leukocyte but suppress adhesion and activation of the platelets has been investigated variously as of today, durability of the coating is also insufficient in addition to the improved effects in removal efficiency of leukocytes and recovery efficiency of platelets.

Means for Solving the Problems

The present inventors have paid attention not to the conventional coating agent which shows adhesion to the leukocyte but suppress adhesion and activation of the platelets, but to a polymer having a phosphoric acid ester group which is expected to be a coating material having a function of inhibiting adhesion of various biological substances including the leukocytes, and have intensively studied. As a result, they have found that a porous element coated at least a part of a surface thereof by a copolymer containing a specific organic group can capture the desired blood components such as the leukocyte, etc., and pass the other blood components without adhesion, by appropriately selecting a size of the fine pore of the porous element, and is useful as a blood filter improved in removal efficiency or recovery efficiency of the desired blood components, whereby the present invention has been accomplished.

That is, the present inventions are as follows:

1. a blood filter comprising
a porous element; and
a copolymer which exists in at least a part of the surface of the porous element, and which contains a recurring unit containing an organic group of the following formula (a) and a recurring unit containing an organic group of the following formula (b):

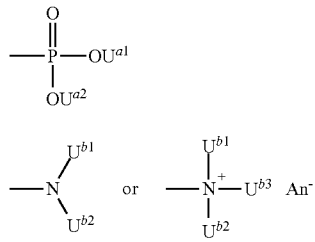

(a)

(b)

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms, and An⁻ represents an anion selected from the group consisting of a halide ion, an inorganic acid ion, a hydroxide ion and an isothiocyanate ion);

2. the blood filter described in the above-mentioned 1, wherein the recurring units containing organic groups of the formulae (a) and (b) are recurring units derived from monomers of the following formulae (A) and (B), respectively:

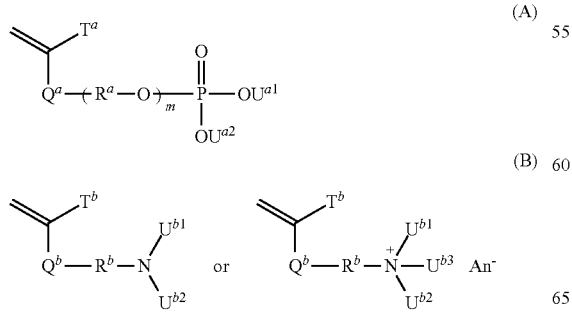

(A)

(B)

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), An⁻ represents an anion selected from the group consisting of a halide ion, an inorganic acid ion, a hydroxide ion and an isothiocyanate ion, and m is an integer of 0 to 6);

3. the blood filter described in the above-mentioned 2, wherein m is 1, and $R^a$ and $R^b$ each independently represent an ethylene group or a propylene group;

4. the blood filter described in any one of the above-mentioned 1 to 3, wherein the copolymer further contains a crosslinked structure derived from a monomer of the following formula (C) or (D):

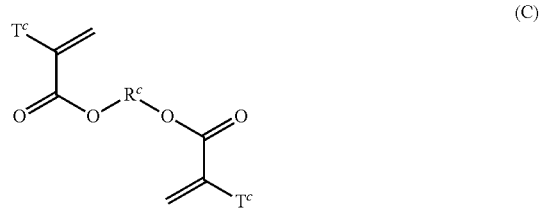

(C)

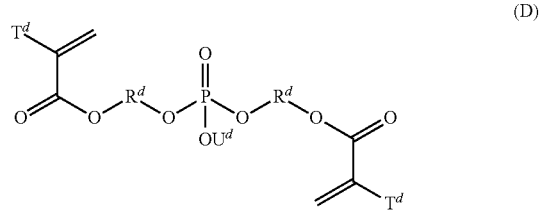

(D)

(wherein $T^c$, $T^d$ and $U^d$ each independently represent a hydrogen atom or a linear or branched alkyl group having 1 to 5 carbon atoms, $R^c$ and $R^d$ each independently represent a linear or branched alkylene group having 1 to 10 carbon atoms which may be substituted by a halogen atom(s));

5. the blood filter described in the above-mentioned 4, wherein $T^c$ and $T^d$ each independently represent a hydrogen atom or a methyl group, $U^d$ represents a hydrogen atom, and $R^c$ and $R^d$ each independently represent an ethylene group or a propylene group;

6. the blood filter described in any one of the above-mentioned 1 to 5, wherein the porous element is nonwoven fabric;

7. a method for manufacturing a blood filter which comprises
a process of coating a copolymer which contains a recurring unit containing an organic group of the following formula (a) and a recurring unit containing an organic group of the following formula (b):

(a)

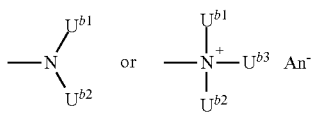
(b)

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms, and $An^-$ represents an anion selected from the group consisting of a halide ion, an inorganic acid ion, a hydroxide ion and an isothiocyanate ion), onto at least a part of a surface of a porous element; and a process of drying the coated porous element at −200° C. to 200° C.;

8. the manufacturing method described in the above-mentioned 7, wherein the recurring units containing organic groups of the formulae (a) and (b) are recurring units derived from monomers of the following formulae (A) and (B), respectively:

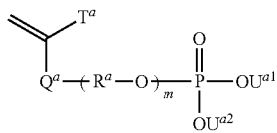
(A)

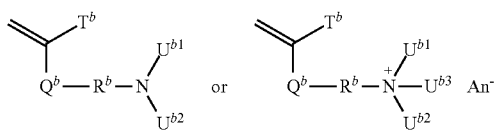
(B)

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), $An^-$ represents an anion selected from the group consisting of a halide ion, an inorganic acid ion, a hydroxide ion and an isothiocyanate ion, and m is an integer of 0 to 6);

9. the manufacturing method described in the above-mentioned 7 or 8, wherein the coating process is carried out by using a varnish containing the copolymer;

10. the manufacturing method described in the above-mentioned 9, wherein the varnish containing the copolymer is previously adjusted a pH;

11. the manufacturing method described in any one of the above-mentioned 7 to 10, wherein a process of washing the coated porous element is further contained before and/or after the drying process;

12. the manufacturing method described in the above-mentioned 11, wherein the washing process after drying is carried out by using at least one solvent selected from the group consisting of water and an aqueous solution containing an electrolyte(s).

Effect of the Invention

The blood filter of the present invention can capture the desired blood components alone by using a porous element at least a part of the surface of which is coated by a copolymer containing a specific organic group, and by appropriately selecting a size of the fine pore of the porous element. In particular, the blood filter of the present invention is a leukocyte removing filter, which is improved in removal efficiency of leukocytes and recovery efficiency of platelets by using a porous element at least a part of a surface of which is coated by a copolymer containing a specific organic group, and appropriately selecting a size (preferably an average pore diameter is 20 μm or less) of fine pores of the porous element whereby it can capture the leukocytes but pass the other blood components without adhesion. In addition, the captured leukocyte may be recovered and used. Further, in the blood filter of the present invention, at least a part of the surface of the porous element has been coated by a copolymer containing an anion of the formula (a) and a cation of the formula (b), so that due to the electrostatic balance of the cation and the anion, the surface of the porous element is maintained to electrically neutral whereby adhesion of the blood components can be considered to be prevented. On the other hand, by forming an ion bonding (ion complex) with the cation and the anion in the coating, it can be firmly fixed irrespective of a kind of the substrate such as glass, fiber, inorganic particles and a resin (synthetic resin and natural resin), and further, after fixing, it becomes a coating excellent in durability against an aqueous solvent (water, a phosphate buffered solution (PBS), an alcohol, etc.). That is, according to the present invention, a blood filter excellent in durability in addition to removal efficiency of leukocytes and recovery efficiency of platelets can be provided.

EMBODIMENTS TO CARRY OUT THE INVENTION

Figure 1:
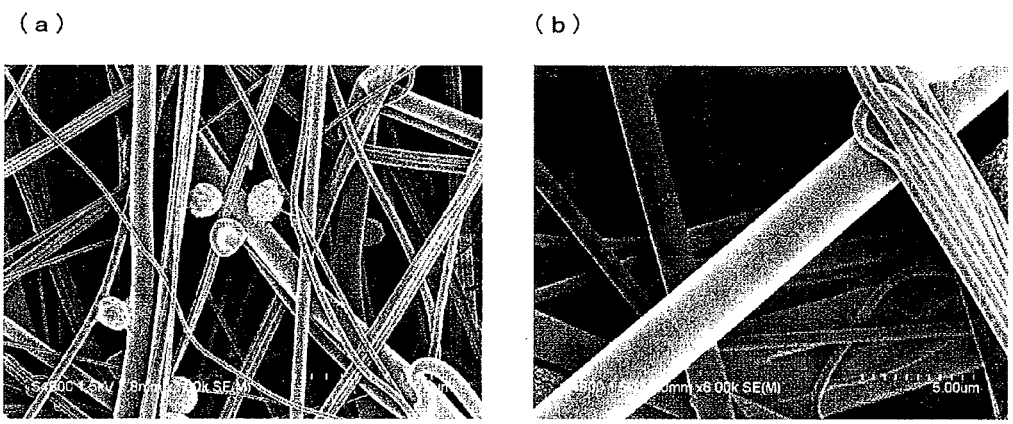
FIG. 1(a) is a scanning type electron microscope (SEM) image (magnification: 2,000-fold) of the blood filter of Example 3 after used in Test example 1.
FIG. 1(b) is an SEM image (magnification: 6,000-fold) in which a part of (a) is enlarged.

Examples of the blood in the present invention include peripheral blood, bone marrow and cord blood.

Also, as the leukocyte to be removed or recovered by the blood filter of the present invention, there may be mentioned granulocyte, neutrophils, basophils, eosinophils, lymphocytes, T lymphocytes, helper T lymphocytes, cytotoxic T lymphocytes, suppressor T lymphocytes, B lymphocytes, plasma cells, NK cells, monocytes, dendritic cells, fat cells, mononucleosis, hematopoietic precursor cells, hematopoietic stem cells, myeloblasts, leukemia cells, etc.

<<Blood Filter>>

The first embodiment of the present invention is directed to a blood filter comprising a porous element; and a copolymer which exists in at least a part of the surface of the porous element, and which contains a recurring unit containing an organic group of the following formula (a) and a recurring unit containing an organic group of the following formula (b):

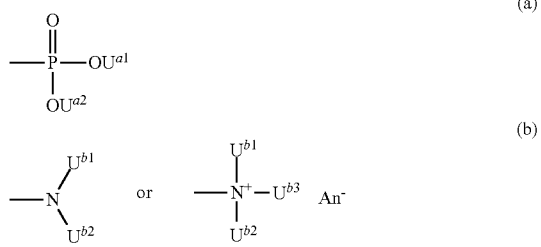

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms, and $An^-$ represents an anion selected from the group consisting of a halide ion, an inorganic acid ion, a hydroxide ion and an isothiocyanate ion).

<Porous Element>

"The porous element" which can be used for the blood filter of the present invention means a sheet state or a granular state (a bead state) porous structure having continuous fine pores. Such a porous structure may be any of the forms of the conventionally known filter materials, and an example thereof may be mentioned a fibrous porous material such as nonwoven fabric, woven fabric, kilted fabric, fiber mass or a non-fibrous porous material having three-dimensional network continuous fine pores such as a sponge state porous material, a porous membrane, a sintered body of particles, etc. The porous element is preferably nonwoven fabric in the points of easiness in handling and availability, and a low cost.

As the raw material of the porous element, for example, glass, a metal containing compound or a semi-metal containing compound, an activated charcoal or a resin may be used.

The metal containing compound or the semi-metal containing compound may be mentioned, for example, ceramics comprising a metal oxide as a basic component, which are a sintered body baked by a heat treatment at a high temperature, a semi-conductor such as silicon, an inorganic solid material including a molded product of an inorganic compound such as a metal oxide or a semimetal oxide (silicon oxide, alumina, etc.), a metal carbide or a semi-metal carbide, a metal nitride or a semi-metal nitride (silicon nitride, etc.), a metal boride or a semi-metal boride, aluminum, nickel-titanium and stainless (SUS304, SUS316, SUS316L, etc.).

The above-mentioned resin may be either a natural resin or a synthetic resin, and the natural resin may be mentioned, for example, cellulose, cellulose triacetate (CTA), cellulose to which dextran sulfate has been fixed, etc., while the synthetic resin may be mentioned, for example, a polyacrylonitrile (PAN), a polyester-based polymer alloy (PEPA), a polystyrene (PS), a polysulfone (PSF), a polyethylene terephthalate (PET), a polymethyl methacrylate (PMMA), a polyvinyl alcohol (PVA), a polyurethane (PU), ethylene vinyl alcohol (EVAL), a polyethylene (PE), a polyester (PE), a polypropylene (PP), a polyvinylidene fluoride (PVDF), various kinds of ion exchange resins or a polyether sulfone (PES), etc. In the blood filter of the present invention, no treatment at the high temperature is required for coating the copolymer onto at least a part of the surface of the porous element to be present, so that a resin having low heat resistance, etc., can be applied thereto.

In particular, a raw material of the fibrous porous material may be exemplified by a synthetic fiber such as a polyamide, an aromatic polyamide, a polyester, a polyacrylonitrile, a polytrifluorochloroethylene, a polystyrene, a polymethyl (meth)acrylate, a polyethylene, a polypropylene, a poly-4-methylpentene, and a regenerated fiber such as cellulose, cellulose acetate.

The non-fibrous porous material may be exemplified by a porous material such as a polyethylene, a polypropylene, a poly-4-methylpentene, a polyvinylformal, a polyacrylonitrile, a polysulfone, cellulose, cellulose acetate, a polyurethane, a polyvinyl acetal, a polyester, a polyamide, a polyether imide, a poly(meth)acrylate, a polyvinylidene fluoride, a polyimide.

A size of the fine pore of the porous element can be appropriately selected depending on the size of the blood component to be captured or recovered. For example, when the blood filter is a leukocyte removing filter, a size of the fine pore sufficient for capturing (or recovering) the leukocyte, and passing through the other blood components may be selected. For example, a size of the fine pore for the leukocyte removing filter is an average pore diameter of 20 µm or less, preferably an average pore diameter of 1 to 20 µm. The average pore diameter can be calculated from, for example, an electron microscopic photograph, etc.

<Copolymer>

The blood filter of the present invention comprises at least one part of the surface of the porous element being coated by a specific copolymer. The copolymer according to the present invention is a copolymer which contains a recurring unit containing an organic group of the following formula (a) and a recurring unit containing an organic group of the following formula (b):

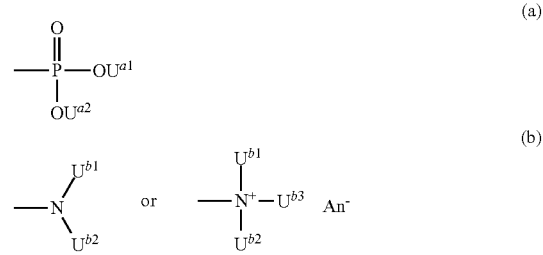

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms, and $An^-$ represents an anion selected from the group consisting of a halide ion, an inorganic acid ion, a hydroxide ion and an isothiocyanate ion).

The copolymer according to the present invention is not particularly limited so long as it is a copolymer which contains a recurring unit containing an organic group of the above-mentioned formula (a) and a recurring unit containing an organic group of the above-mentioned formula (b). The copolymer is desirably a material obtained by subjecting a monomer containing an organic group of the above-mentioned formula (a) and a monomer containing an organic group of the above-mentioned formula (b) to radical polymerization, and a material obtained by polycondensation or polyaddition reaction may be used. Examples of the copolymer include a vinyl polymerized polymer in which an olefin(s) is/are reacted, a polyamide, a polyester, a polycarbonate, a polyurethane, and among these, a vinyl polymerized polymer in which an olefin(s) is/are reacted or a (meth)acrylic polymer in which a (meth)acrylate compound(s) is/are polymerized is desired. Further, in the present invention, the (meth)acrylate compound means both of an acrylate compound and a methacrylate compound. For example, a (meth)acrylic acid means an acrylic acid and a methacrylic acid.

The monomer containing the organic groups of the above-mentioned formulae (a) and (b) are preferably monomers of the following formulae (A) and (B), respectively:

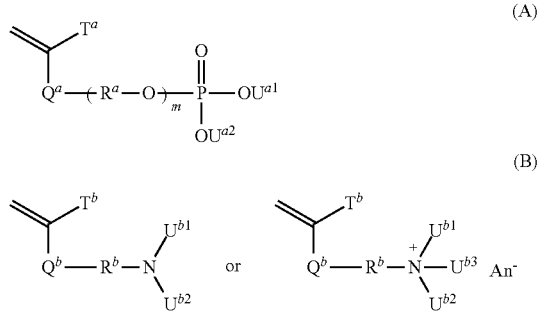

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), $An^-$ represents an anion selected from the group consisting of a halide ion, an inorganic acid ion, a hydroxide ion and an isothiocyanate ion, and m is an integer of 0 to 6). Accordingly, the recurring units derived from the monomers of the formulae (A) and (B) are of the following formulae (a1) and (b1), respectively:

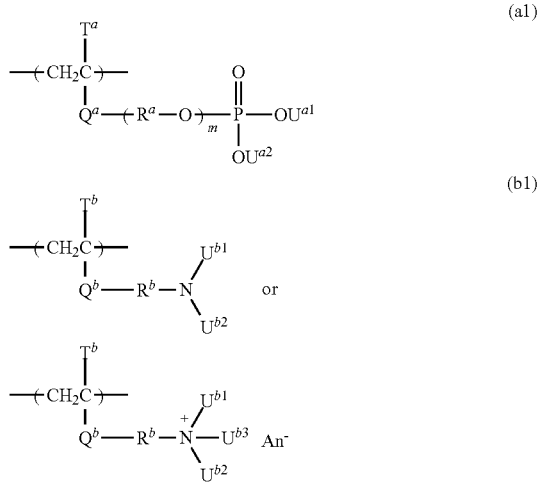

(wherein $T^a$, $T^b$, $U^{a1}$, $U^{a2}$, $U^{b1}$, $U^{b2}$ and $U^{b3}$, $Q^a$ and $Q^b$, $R^a$ and $R^b$, $An^-$ and m are the same as defined above).

In the present invention, "the linear or branched alkyl group having 1 to 5 carbon atoms" may be mentioned, for example, a methyl group, an ethyl group, an n-propyl group, an isopropyl group, an n-butyl group, an isobutyl group, a s-butyl group, a t-butyl group, an n-pentyl group, a 1-methylbutyl group, a 2-methylbutyl group, a 3-methylbutyl group, a 1,1-dimethylpropyl group, a 1,2-dimethylpropyl group, a 2,2-dimethylpropyl group or a 1-ethylpropyl group.

In the present invention, "the ester bond" means —C(=O)—O— or —O—C(=O)—, and "the amide bond" means —NHC(=O)— or —C(=O)NH—.

In the present invention, "the linear or branched alkylene group having 1 to 10 carbon atom which may be substituted by a halogen atom(s)" means a linear or branched alkylene group having 1 to 10 carbon atoms or a linear or branched alkylene group having 1 to 10 carbon atoms substituted by one or more halogen atoms. Here, "the linear or branched alkylene group having 1 to 10 carbon atoms" is a divalent organic group in which a hydrogen atom is further removed from the above-mentioned alkyl group and may be mentioned, for example, a methylene group, an ethylene group, a propylene group, a trimethylene group, a tetramethylene group, a 1-methylpropylene group, a 2-methylpropylene group, a dimethylethylene group, an ethylethylene group, a pentamethylene group, a 1-methyl-tetramethylene group, a 2-methyl-tetramethylene group, a 1,1-dimethyl-trimethylene group, a 1,2-dimethyl-trimethylene group, a 2,2-dimethyl-trimethylene group, a 1-ethyl-trimethylene group, a hexamethylene group, an octamethylene group and a decamethylene group, etc. Among these, an ethylene group, a propylene group, an octamethylene group and a decamethylene group are preferred, a linear or branched alkylene group having 1 to 5 carbon atoms including, for example, an ethylene group, a propylene group, a trimethylene group and a tetramethylene group are more preferred, and an ethylene group or a propylene group is particularly preferred. "The linear or branched alkylene group having 1 to 10 carbon atoms substituted by one or more halogen atoms" means a group in which one or more optional hydrogen atoms of the above-mentioned alkylene group is/are substituted by a halogen atom(s), and particularly preferred is a group in which a part or whole of the hydrogen atoms of an ethylene group or a propylene group is/are substituted by a halogen atom(s).

In the present invention, "the halogen atom" may be mentioned a fluorine atom, a chlorine atom, a bromine atom and an iodine atom.

In the present invention, "the halide ion" means an anion of a halogen atom, and may be mentioned a fluoride ion, a chloride ion, a bromide ion and an iodide ion, preferably a chloride ion.

In the present invention, "the inorganic acid ion" means a carbonate ion, a sulfate ion, a phosphate ion, a hydrogen phosphate ion, a dihydrogen phosphate ion, a nitrate ion, a perchlorate ion or a borate ion.

As the above-mentioned $An^-$, preferred are a halide ion, a sulfate ion, a phosphate ion, a hydroxide ion and an isothiocyanate ion, and particularly preferred is a halide ion.

In the formulae (A) and (B), $T^a$ and $T^b$ are preferably each independently a hydrogen atom, a methyl group or an ethyl group, and more preferably each independently a hydrogen atom or a methyl group.

In the formula (a), the formula (b), and the formulae (A) and (B), $U^{a1}$, $U^{a2}$, $U^{b1}$, $U^{b2}$ and $U^{b3}$ are preferably each independently a hydrogen atom, a methyl group or an ethyl group. In the formula (a) and the formula (A), $U^{a1}$ and $U^{a2}$ are more preferably a hydrogen atom. In the formulae (b)

and (B), $U^{b1}$, $U^{b2}$ (and $U^{b3}$) are more preferably a methyl group or an ethyl group, and particularly preferably a methyl group.

In the formulae (A) and (B), $Q^a$ and $Q^b$ preferably each independently represent an ester bond (—C(=O)—O— or —O—C(=O)—) or an amide bond (—NHC(=O)— or —C(=O)NH—), more preferably each independently represent —C(=O)—O— or —C(=O)NH—, particularly preferably —C(=O)—O—.

In the formulae (A) and (B), $R^a$ and $R^b$ preferably each independently represent a linear or branched alkylene group having 1 to 3 carbon atoms which may be substituted by a halogen atom(s), more preferably each independently represent an ethylene group or a propylene group, or an ethylene group or a propylene group substituted by one chlorine atom, particularly preferably an ethylene group or a propylene group.

In the formulae (A) and (B), m is preferably an integer of 0 to 3, more preferably an integer of 1 or 2, particularly preferably 1.

Specific examples of the above-mentioned formula (A) include vinyl phosphonic acid, acid phosphoxyethyl(meth)acrylate, 3-chloro-2-acid phosphoxypropyl(meth)acrylate, acid phosphoxypropyl(meth)acrylate, acid phosphoxymethyl(meth)acrylate, acid phosphoxypolyoxyethylene glycol mono(meth)acrylate, acid phosphoxypolyoxypropylene glycol mono(meth)acrylate, and among these, vinyl phosphonic acid, acid phosphoxyethyl methacrylate (=2-(methacryloyloxy)ethyl phosphate) is preferably used.

The structural formulae of the vinyl phosphonic acid, acid phosphoxyethyl methacrylate (=2-(methacryloyloxy)ethyl phosphate) and acid phosphoxypolyoxyethylene glycol monomethacrylate are shown by the following formula (A-1) to the formula (A-3), respectively.

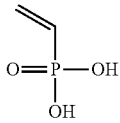

(A-1)

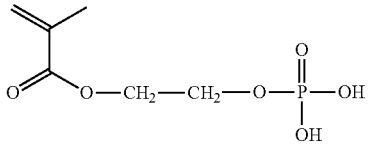

(A-2)

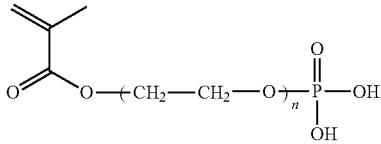

(A-3)

$n = 4{\sim}5$

These compounds may contain a (meth)acrylate compound having two functional groups of the formula (C) or (D) mentioned later at the time of synthesis in some cases.

Specific examples of the above-mentioned formula (B) include dimethylaminoethyl(meth)acrylate, diethylaminoethyl(meth)acrylate, dimethylaminopropyl(meth)acrylate, 2-(t-butylamino)ethyl(meth)acrylate, methacryloylcholine chloride, and among these, dimethylaminoethyl(meth)acrylate, methacryloylcholine chloride or 2-(t-butylamino)ethyl(meth)acrylate is preferably used.

Structural formulae of the dimethylaminoethyl acrylate (=acrylic acid 2-(dimethylamino)ethyl), dimethylaminoethyl methacrylate (=methacrylic acid 2-(dimethylamino)ethyl), methacryloylcholine chloride and 2-(t-butylamino)ethyl methacrylate (=methacrylic acid 2-(t-butylamino)ethyl are shown by the following formula (B-1) to the formula (B-4), respectively.

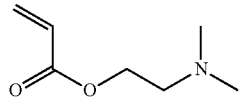

(B-1)

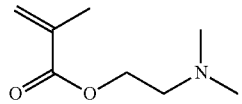

(B-2)

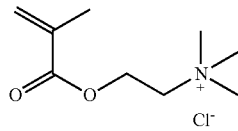

(B-3)

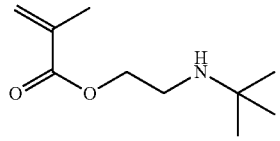

(B-4)

A ratio of the recurring unit containing an organic group of the formula (a) (or a recurring unit of the formula (a1)) in the above-mentioned copolymer is 20 mol % to 80 mol %, preferably 30 mol % to 70 mol %, more preferably 40 mol % to 60 mol %. Further, the copolymer according to the present invention may contain two or more kinds of the recurring unit containing an organic group of the formula (a) (or the recurring units of the formula (a1)).

A ratio of the recurring unit containing an organic group of the formula (b) (or a recurring unit of the formula (b1)) in the above-mentioned copolymer according to the present invention may be the whole remainder subtracting the ratio of the above-mentioned formula (a) (or the formula (a1)) from the whole of the copolymer, or may be the remainder subtracting the total ratio of the above-mentioned formula (a) (or the formula (a1)) and a third component mentioned below from the same. Further, the copolymer according to the present invention may contain two or more kinds of the recurring units containing an organic group of the formula (b) (or a recurring unit of the formula (b1)).

Further, the copolymer according to the present invention may be further copolymerized with an optional third component. For example, as the third component, a (meth)acrylate compound having two or more functional groups may be copolymerized, and a part of the polymer may be partially three-dimensionally crosslinked. Such a third component may be mentioned, for example, a bifunctional monomer of the following formula (C) or (D):

(C)

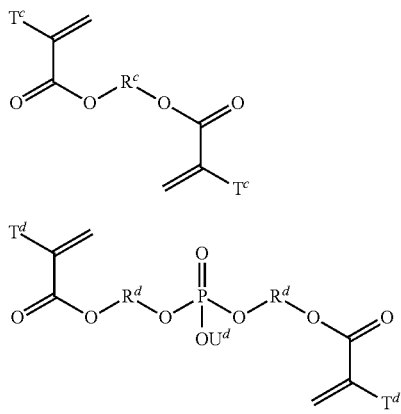

(D)

(wherein $T^c$, $T^d$ and $U^d$ each independently represent a hydrogen atom or a linear or branched alkyl group having 1 to 5 carbon atoms, $R^c$ and $R^d$ each independently represent a linear or branched alkylene group having 1 to 10 carbon atoms which may be substituted by a halogen atom(s)). That is, the copolymer according to the present invention may preferably contain a crosslinked structure derived from such a bifunctional monomer.

In the formulae (C) and (D), $T^c$ and $T^d$ are preferably each independently a hydrogen atom, a methyl group or an ethyl group, and more preferably each independently a hydrogen atom or a methyl group.

In the formulae (C) and (D), $U^d$ is preferably a hydrogen atom, a methyl group or an ethyl group, more preferably a hydrogen atom.

In the formulae (C) and (D), $R^c$ and $R^d$ each preferably independently represent a linear or branched alkylene group having 1 to 3 carbon atoms which may be substituted by a halogen atom(s), more preferably each independently represent an ethylene group or a propylene group, or an ethylene group or a propylene group substituted by one chlorine atom, particularly preferably an ethylene group or a propylene group.

The bifunctional monomer of the formula (C) may be preferably mentioned ethylene glycol di(meth)acrylate, triethylene glycol di(meth)acrylate, propylene glycol di(meth)acrylate, etc. The bifunctional monomer of the formula (D) may be preferably mentioned bis[(2-methacryloyloxy)methyl]phosphate, bis[(2-methacryloyloxy)ethyl]phosphate, bis[(2-methacryloyloxy)propyl]phosphate, etc.

The optional third component may be a trifunctional monomer. Such a trifunctional monomer as the third component may be mentioned, for example, phosphynylidine tris(oxy-2,1-ethane diyl)triacrylate.

Among these, ethylene glycol di(meth)acrylate of the following formula (C-1) and bis[2-(methacryloyloxy)ethyl] phosphate of the following formula (D-1) are particularly preferred.

(C-1)

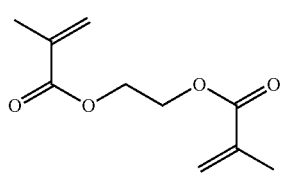

(D-1)

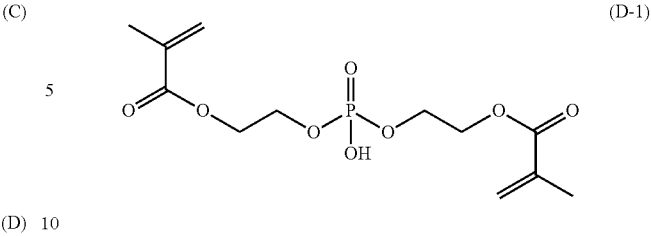

One or two or more kinds of these third components may be contained in the copolymer. Among the above-mentioned compounds, the bifunctional monomer of the formula (D) is preferred, and the bifunctional monomer of the formula (D-1) is particularly preferred.

A ratio of the third component in the above-mentioned copolymer, for example, the cross-linked structure derived from the bifunctional monomer of the above-mentioned formula (C) or (D) is 0 mol % to 50 mol %.

<Manufacturing Method of Copolymer>

As the synthetic method of the copolymer according to the present invention, they can be synthesized by the methods such as the radical polymerization, the anion polymerization, the cation polymerization which are general synthetic methods of an acrylic polymer or a methacrylic polymer, etc. As the reaction form thereof, various methods such as the solution polymerization, the suspension polymerization, the emulsion polymerization, the bulk polymerization may be employed.

As the solvent for the reaction, it may be water, a phosphate buffered solution or an alcohol such as ethanol, etc., or a mixed solution in which these solvents are used in combination, and desirably contains water or ethanol. Further, it is preferred to contain water or ethanol in an amount of 10% by mass or more and 100% by mass or less. Moreover, it is preferred to contain water or ethanol in an amount of 50% by mass or more and 100% by mass or less. Furthermore, it is preferred to contain water or ethanol in an amount of 80% by mass or more and 100% by mass or less. Still further, it is preferred to contain water or ethanol in an amount of 90% by mass or more and 100% by mass or less. A total amount of water and ethanol is preferably 100% by mass.

As the reaction concentration, for example, it is preferred to make the concentration of the monomer containing an organic group of the above-mentioned formula (a) and the monomer containing an organic group of the above-mentioned formula (b) in the reaction solvent 0.01% by mass to 4% by mass. If the concentration is 4% by mass or more, for example, there is sometimes a case that the copolymer is gelled in the reaction solvent due to strong associative property possessed by the phosphate group of the formula (a). If the concentration is 0.01% by mass or less, the concentration of the obtained varnish is too low, it is difficult to prepare the composition for forming a coating film for obtaining a coating film having a sufficient film thickness. The concentration is more preferably 0.01% by mass to 3% by mass, for example, 3% by mass or 2% by mass.

In the synthesis of the copolymer according to the present invention, for example, after preparing an acidic phosphoric acid ester monomer (half salt) of the formula (1), it may be polymerized to prepare the copolymer.

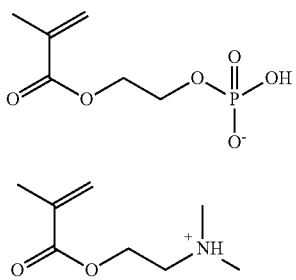

The phosphate group-containing monomer is a monomer easily associated, so that it may be added dropwise to the reaction solvent little by little so as to rapidly disperse therein when it is added dropwise to the reaction system. Further, the reaction solvent may be heated (for example, 40° C. to 100° C.) to increase the solubility of the monomer and the polymer.

To proceed with the polymerization reaction efficiently, a polymerization initiator is desirably used. Examples of the polymerization initiator to be used include 2,2'-azobis (isobutyronitrile), 2,2'-azobis(2-methylbutyronitrile), 2,2'-azobis(2,4-dimethylvaleronitrile), 4,4'-azobis(4-cyanovaleric acid), 2,2'-azobis(4-methoxy-2,4-dimethylvaleronitrile), 1,1'-azobis(cyclohexan-1-carbonitrile), 1-[(1-cyano-1-methyl-ethyl)azo]formamide, 2,2'-azobis[2-(2-imidazolin-2-yl)propane]dihydrochloride, 2,2'-azobis[2-(2-imidazolin-2-yl)propane], 2,2'-azobis(2-methylpropionamidine)dihydrochloride, 2,2'-azobis[(2-methyl-N-(2-hydroxyethyl)propionamide] (available from Wako Pure Chemical Industries, Ltd., VA-086, 10-hr half-life temperature; 86° C.), benzoyl peroxide (BPO), 2,2'-azobis(N-(2-carboxyethyl)-2-methylpropionamidine) n-hydrate (available from Wako Pure Chemical Industries, Ltd., VA-057, 10-hr half-life temperature; 57° C.), 4,4'-azobis(4-cyanopentanoic acid) (available from Wako Pure Chemical Industries, Ltd., VA-501), 2,2'-azobis[2-(2-imidazolidin-2-yl)propane]dihydrochloride (available from Wako Pure Chemical Industries, Ltd., VA-044, 10-hr half-life temperature; 44° C.), 2,2'-azobis[2-(2-imidazolidin-2-yl)propane] disulfate dihydrate (available from Wako Pure Chemical Industries, Ltd., VA-046B, 10-hr half-life temperature; 46° C.), 2,2'-azobis[2-(2-imidazolidin-2-yl)propane] (available from Wako Pure Chemical Industries, Ltd., VA-061, 10-hr half-life temperature; 61° C.), 2,2'-azobis(2-amidinopropane)dihydrochloride (available from Wako Pure Chemical Industries, Ltd., V-50, 10-hr half-life temperature; 56° C.), peroxodisulfate or t-butyl hydroperoxide, and among these, taking ion balance and solubility in water into consideration, it is desired to use any of 2,2'-azobis[(2-methyl-N-(2-hydroxyethyl)propionamide], 2,2'-azobis[N-(2-carboxyethyl)-2-methylpropionamidine] n-hydrate, 4,4'-azobis(4-cyanopentanoic acid), 2,2'-azobis[2-(2-imidazolidin-2-yl) propane]dihydrochloride, 2,2'-azobis[2-(2-imidazolidin-2-yl)propane]disulfate dihydrate, 2,2'-azobis[2-(2-imidazolidin-2-yl)propane], 2,2'-azobis(2-amidinopropane) dihydrochloride and peroxodisulfate.

An amount of the polymerization initiator to be added is 0.05% by mass to 10% by mass based on the total weight of the monomer to be used for the polymerization.

As the reaction conditions, the polymerization reaction proceeds by heating a reaction vessel by an oil bath, etc., at 50° C. to 200° C. and stirring for 1 hour to 48 hours, more preferably at 80° C. to 150° C. for 5 hours to 30 hours to obtain the copolymer of the present invention. The reaction atmosphere is preferably a nitrogen atmosphere. As the reaction procedure, the whole reaction substances are charged in the reaction solvent at the room temperature, and then, the polymerization may be carried out by heating to the above-mentioned temperature, or whole or a part of the mixture of the reaction substances may be added dropwise to the previously heated solvent little by little.

For example, as the latter reaction procedure, a mixture containing the compounds of the above-mentioned formulae (A) and (B), a solvent and a polymerization initiator is added dropwise into a solvent which has been maintained at a temperature higher than a 10-hr half-life temperature of the polymerization initiator to react (polymerize) the reactants. By employing such a reaction procedure and temperature conditions, a concentration of the compounds of the above-mentioned formulae (A) and (B) in the reaction solvent can be made, for example, 0.01% by mass to 10% by mass. In this embodiment, even if the concentration exceeds 4% by mass, the dropping phase and the reaction phase become a transparent uniform solution before the reaction, and gelation of the copolymer in the reaction solvent after the reaction can be suppressed.

A molecular weight of the copolymer according to the present invention may be several thousand to several million or so, preferably 5,000 to 5,000,000. It is more preferably 10,000 to 2,000,000. Also, it may be either of a random copolymer, a block copolymer or a graft copolymer, there is no specific limitation in the copolymerization reaction itself for manufacturing the copolymer, and a conventionally known method synthesized in a solution such as radical polymerization, ion polymerization, or polymerization utilizing photopolymerization, macromer or emulsion polymerization can be used. Depending on the purposes thereof to be used, any one of the copolymers of the present invention may be used solely, or plural kinds of the copolymers may be used by mixing with appropriately changing the ratios thereof.

The various copolymers manufactured as mentioned above may be a two-dimensional polymer or a three-dimensional polymer, and is in a state of dispersing in a solution containing water. That is, in the varnish containing these polymers, it is not preferred to cause ununiform gelation or turbid precipitation, and a transparent varnish, a dispersed colloidal varnish or a sol is preferred.

<<Manufacturing Method of Blood Filter>>

The second embodiment of the present invention is directed to a method for manufacturing a blood filter which comprises a process of coating a copolymer which contains a recurring unit containing an organic group of the following formula (a) and a recurring unit containing an organic group of the following formula (b):

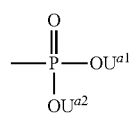

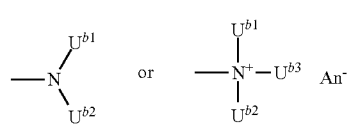

(wherein $U^{a1}$, $U^{a2}$, $U^{b1}$, $U^{b2}$ and $U^{b3}$, and $An^-$ have the same meanings as defined above) onto at least a part of a surface of a porous element; and a process of drying the coated porous element at −200° C. to 200° C.

<Coating Process>

In the coating process of the method for manufacturing the blood filter of the present invention, the copolymer is coated onto at least a part of the surface of the porous element. Here, the porous element and the copolymer are the same as mentioned in the above items <Porous element> and <Copolymer>, respectively.

The coating process is not specifically limited, and may be carried out by any coating means (for example, coating, dipping, etc.) well known for those skilled in the art, which can contact the porous element with the copolymer. For example, it can be carried out by coating the varnish containing the copolymer to the porous element, or by dipping the porous element into the varnish containing the copolymer. It can be preferably carried out by dipping the porous element into the varnish containing the copolymer.

The varnish containing the copolymer may be prepared by dissolving the copolymer obtained in the above-mentioned item <Manufacturing method of copolymer> in a suitable solvent with a desired concentration, or else, the reaction solution containing the copolymer obtained by such a manufacturing method may be used as a varnish as such or after diluting to a desired solid content. The solvent to be contained in the varnish may be mentioned water, a phosphate buffered solution (PBS) and an alcohol. Examples of the alcohol include an alcohol having 2 to 6 carbon atoms, such as ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol (=neopentyl alcohol), 2-methyl-1-propanol, 2-methyl-1-butanol, 2-methyl-2-butanol (=t-amyl alcohol), 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol and cyclohexanol. The solvent may be used alone or a mixed solvent of a combination thereof, and preferably selected from water, PBS and ethanol. For dissolving the copolymer, water is necessarily contained.

A concentration of the copolymer in the varnish is 0.01 to 4% by mass, more desirably 0.01 to 3% by mass, further desirably 0.01 to 2% by mass, and still further desirably 0.01 to 1% by mass. If the concentration of the copolymer is 0.01% by mass or less, a coating film having a sufficient film thickness cannot be formed, while if it is 4% by mass or more, storage stability of the varnish is poor, and there is a possibility of causing deposition of the dissolved material or gelation thereof.

Further, to the varnish may be added other substances within the range which does not impair the performance of the obtainable coating depending on the necessity, in addition to the above-mentioned copolymer and the solvent. The other substances may be mentioned an antiseptic, a surfactant, a primer which heighten adhesiveness with the substrate (the porous element), an antifungal agent and a saccharide, etc.

To control ion balance of the copolymer in the varnish, a pH of the varnish containing the copolymer may be previously adjusted. The pH adjustment may be carried out, for example, by adding a pH adjusting agent to the varnish containing the copolymer, to make the pH of the varnish 3.5 to 8.5, more preferably 4.0 to 8.0. A kind of the pH adjusting agent which can be used and an amount thereof are appropriately selected depending on the concentration of the copolymer in the varnish, and an existing ratio of the anion and the cation of the copolymer, etc. Examples of the pH adjusting agent include an organic amine such as ammonia, diethanolamine, pyridine, N-methyl-D-glucamine, tris(hydroxymethyl)aminomethane; an alkali metal hydroxide such as potassium hydroxide, sodium hydroxide; an alkali metal halide such as potassium chloride, sodium chloride; an inorganic acid such as sulfuric acid, phosphoric acid, hydrochloric acid, carbonic acid or an alkali metal salt thereof; a quaternary ammonium cation such as choline, or a mixture thereof (for example, a buffer such as a phosphate buffered physiological saline). Among these, ammonia, diethanolamine, N-methyl-D-glucamine, tris(hydroxymethyl)aminomethane, sodium hydroxide and choline are preferred, and ammonia, diethanolamine, sodium hydroxide and choline are particularly preferred.

Such a varnish containing the copolymer is contacted with the porous element to form a coating onto at least a part of the surface thereof. The coating is desirably formed over the whole surface of the porous element.

Further, before the coating process, the surface of the porous element may be washed by applying it to the conventionally known UV/ozone treatment. Such a washing process can be carried out by using a commercially available UV/ozone cleaner, etc.

<Drying and Washing Process>

After the coating process, the coated porous element is dried at a temperature of −200° C. to 200° C. According to the drying, the solvent in the above-mentioned composition for forming the coating film is removed, as well as the formula (a) and the formula (b) of the copolymer according to the present invention form an ion bonding to each other whereby the film is completely and firmly fixed to the substrate. A film thickness of the coating film of the blood filter of the present invention is preferably 10 to 1,000 Å, more preferably 10 to 500 Å. The present inventors have found that according to the manufacturing method of the blood filter of the present invention, a coating having desired characteristics is formed onto the surface of the porous element by a treatment at a low temperature without requiring a treatment at a high temperature, and yet, in spite of a thin film thickness of several ten to several hundred Å or so, it is excellent in durability.

The drying may be carried out, for example, at room temperature (10° C. to 35° C., for example, 25° C.), and for forming a coating film more rapidly, it may be carried out, for example, at 40° C. to 50° C. In addition, a drying process at a very low temperature to low temperature (−200° C. to around −30° C.) by a freeze drying method may be used. Freeze drying is called as freeze vacuum drying, and is a method of removing a solvent under a vacuum state by sublimation while generally cooling a material to be dried with a coolant. A general coolant to be used in the freeze drying may be mentioned a mixed medium of dry ice and methanol (−78° C.), liquid nitrogen (−196° C.), etc. More preferred drying temperature is 10° C. to 180° C., and more preferred drying temperature is 25° C. to 150° C.

Further, before and/or after the drying process, the surface of the coated porous element may be washed with an alcohol having 1 to 5 carbon atoms such as ethanol and/or water. Such a washing process may be carried out at a temperature of 0° C. to 60° C., preferably 25° C. (room temperature) to 40° C. for 30 minutes to 48 hours, preferably 1 to 24 hours.

Further, after the drying, to remove impurities, unreacted monomer, etc., remained on the coating film, and further to adjust ion balance of the copolymer in the film, it is desired to wash the film by washing with flowing water or washing with ultrasonic wave, etc., with at least one solvent selected from the group consisting of water and an aqueous solution containing an electrolyte(s). The above-mentioned water and the aqueous solution containing an electrolyte(s) may be heated, for example, within the range of 40° C. to 95° C. The aqueous solution containing an electrolyte(s) is preferably PBS, a physiological saline (a solution containing sodium chloride alone), a Dulbecco's phosphate buffered physiological saline, a Tris buffered physiological saline, a HEPES buffered physiological saline and a Veronal buffered physiological saline, and PBS is particularly preferred.

Even when the coating is washed with an alcohol, water and PBS, etc., it does not elute and is still firmly fixed to the substrate (i.e., the porous element). The formed coating has a function of inhibiting adhesion of various biological substances including leukocytes. Accordingly, the blood filter of the present invention is useful as a blood filter improved in removal efficiency or recovery efficiency of the desired blood components which can capture the desired blood components such as leukocytes and pass through the other blood components without adhesion by appropriately selecting the size of the fine pore of the porous element.

If necessary, the conventionally known sterilization treatment such as γ ray, ethylene oxide, an autoclave may be applied to sterilize the coated porous element.

EXAMPLES

In the following, Synthetic examples, Examples and Test examples in connection with the blood filter and the method for manufacturing the same of the present invention are shown, but these are shown to explain the present invention in more detail, and the present invention is not limited by these.

<Measurement Method of Raw Material Composition>

Measurement of a concentration (% by mass) of each phosphorus-containing compound in a raw material containing a phosphorus-containing compound was carried out by $^{31}$P-NMR. By using the following standard substance, absolute concentrations (absolute % by mass) of each phosphorus-containing compound contained in the raw material was calculated.

(Measurement Conditions)
Mode: Reverse gate decoupling mode (quantitative mode)
Device: Varian 400 MHz
Solvent: $CD_3OD$ (deuterated methanol) (30% by weight)
Rotation number: 0 Hz
Data point: 64,000
Flip angle: 90°
Waiting time: 70 s
Integration times: 16 times, n=4,
Standard substance: trimethylphosphate+$D_2O$ (75% TMP solution was prepared)

Synthetic Example 1

6.00 g of Phosmer M (available from Unichemical Co., Ltd.; a mixture of acid phosphoxyethyl methacrylate (44.2% by mass), bis[2-(methacryloyloxy)ethyl]phosphate (28.6% by mass), and other substances (27.2% by mass)), 4.12 g of 2-(dimethylamino)ethyl methacrylate (available from Tokyo Chemical Industry Co., Ltd.) and 0.24 g of 2,2'-azobis[2-methyl-N-(2-hydroxyethyl)propionamide] (Product name; VA-086, available from Wako Pure Chemical Industries, Ltd.) were dissolved in 446.34 g of pure water and 49.59 g of ethanol, and charged in a recovery flask, and subjected to nitrogen purge by blowing nitrogen thereinto, and then subjected to polymerization reaction in an oil bath at 100° C. for 24 hours to obtain 506.05 g of a varnish containing a copolymer with a solid content of 2% by mass.

Thereafter, to 1.00 g of the varnish containing a copolymer were added 0.90 g of pure water and 0.10 g of ethanol, and then thoroughly stirred to prepare a surface treatment agent (L) (solid content: 1% by mass).

Comparative Synthetic Example 1

0.6 g of N,N-dimethylaminoethyl methacrylate, 15 g of 2-hydroxyethyl methacrylate and 0.03 g of 2,2'-azobis (isobutyronitrile) were dissolved in 62.4 g of ethanol and charged in a recovery flask, and subjected to nitrogen purge by blowing nitrogen thereinto, and then subjected to polymerization reaction in an oil bath at 68° C. for 24 hours to obtain a varnish containing a copolymer with a solid content of 20% by mass.

Thereafter, to 5.00 g of the varnish containing a copolymer were added 95 g of ethanol, and then thoroughly stirred to prepare a surface treatment agent (M) (solid content: 1% by mass).

TABLE 1

| Fixing method | Treatment 1 UV/ozone | Treatment 2 Surface treatment agent | Treatment 3 Drying | Treatment 4 Ethanol | Treatment 5 Water treatment | Treatment 6 Drying |
|---|---|---|---|---|---|---|
| No. 1 | ○ | L | ○ | X | X | X |
| No. 2 | ○ | L | X | X | ○ | ○ |
| No. 3 | ○ | L | ○ | X | ○ | ○ |
| No. 4 | ○ | L | X | ○ | ○ | ○ |
| No. 5 | X | L | ○ | X | ○ | ○ |
| No. 6 | X | X | X | X | X | X |
| No. 7 | X | X | ○ | X | X | X |
| No. 8 | ○ | X | ○ | X | X | X |
| No. 9 | ○ | M | ○ | X | ○ | ○ |
| No. 10 | X | M | ○ | X | ○ | ○ |

Treated: ○
Untreated: X

<Fixing Methods No. 1 to 10>

The respective treatment processes shown below were combined as described in Table 1 to prepare blood filters.
Treatment 1: Nonwoven fabric (see the following Test examples 1 to 5) was surface treated by UV ozone cleaner UV253E (manufactured by Filjohn Inc.);
Treatment 2: Surface treatment agent (L) prepared in Synthetic example 1 or surface treatment agent (M) prepared in Comparative synthetic example 1 was prepared in an amount of 10 g (solid content: 1% by mass) per 0.1 g of nonwoven fabric, and after dipping the nonwoven fabric therein at room temperature for 1 day, excess solution was removed and then air blowing was carried out;
Treatment 3: drying at 40° for 1 day;
Treatment 4: dipping in ethanol for 1 day;
Treatment 5: dipping in water for 1 hour;
Treatment 6: drying at 40° for 1 day.

Test Example 1: Rabbit Blood Filtering Performance of Surface Treatment Agent (L) Fixed to Nonwoven Fabric Made of Polyethylene Terephthalate (PET)

The respective PET nonwoven fabrics (Examples 1 to 5: a basis weight of 38 g/m$^2$, a thickness of 0.2 mm, a fiber diameter of 1 to 2 μm, an air permeability of 10 cc/cm$^2$/sec, an average pore diameter of about 8 μm) subjected to the fixing method (Fixing method Nos. 1 to 5) shown in Table 1 were each punched with a size of φ 25 mm, and three sheets thereof were incorporated into the blood circuit to prepare samples for the blood filtering performance. In Comparative examples, untreated (Fixing methods No. 6 to 8) PET nonwoven fabrics (Comparative examples 1 to 3) were used. As the blood, citrated fresh blood drawn out from a rabbit was used, and 7.5 ml thereof was filtered through each sample. Leukocyte concentrations, platelet concentrations and red blood cell concentrations before filtration and after filtration were each measured by an automatic Hematology Analyzer (manufactured by Sysmex Corporation, XT-2000i), and a leukocyte removing rate, a platelet recovering rate and a red blood cell recovering rate were obtained according to the following formulae. The results are shown in Table 2.

Leukocyte removing rate (%)=100×(1−Number of leukocytes after filtration/Number of leukocytes before filtration)

Red blood cell recovering rate (%)=100×Number of red blood cells after filtration/Number of red blood cells before filtration Platelet recovering rate (%)=100×Number of plasma after filtration/Number of plasma before filtration    [Numerical formula 1]

TABLE 2

(PET nonwoven fabric)

| | Fixing method | Leukocyte removing rate (%) | Red blood cell recovering rate (%) | Platelet recovering rate (%) |
|---|---|---|---|---|
| Example 1 | No. 1 | 85 | 96 | 101 |
| Example 2 | No. 2 | 89 | 98 | 99 |
| Example 3 | No. 3 | 94 | 100 | 97 |
| Example 4 | No. 4 | 83 | 100 | 98 |
| Example 5 | No. 5 | 94 | 100 | 92 |

TABLE 2-continued (PET nonwoven fabric)

| | Fixing method | Leukocyte removing rate (%) | Red blood cell recovering rate (%) | Platelet recovering rate (%) |
|---|---|---|---|---|
| Comparative example 1 | No. 6 | 74 | 97 | 57 |
| Comparative example 2 | No. 7 | 87 | 91 | 51 |
| Comparative example 3 | No. 8 | 89 | 99 | 59 |

Figure 2:
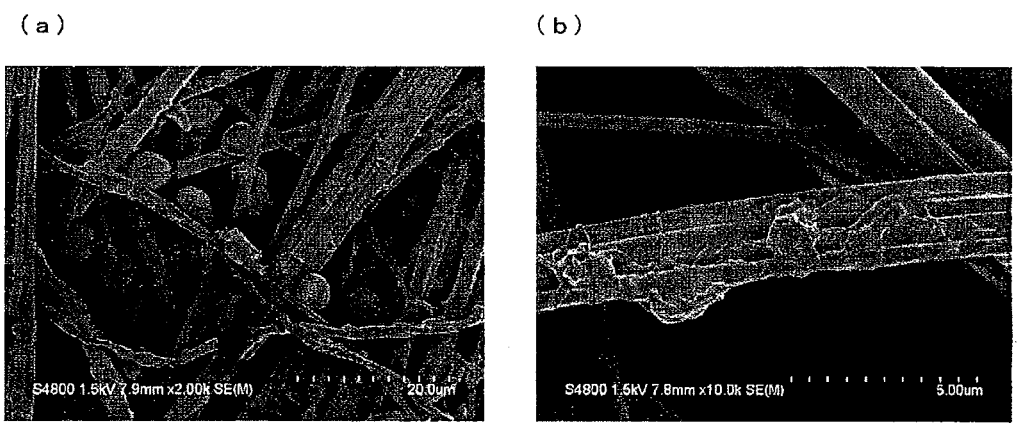
FIG. 2(a) is an SEM image (magnification: 2,000-fold) of the blood filter of Comparative example 1 after used in Test example 1.
FIG. 2(b) is an SEM image (magnification: 10,000-fold) in which a part of (a) is enlarged.

From Table 2, in the PET nonwoven fabrics (Examples 1 to 5) to which the surface treatment agent (L) has been fixed, the platelet recovering ability was clearly improved while maintaining the leukocyte removing ability as compared with those of Comparative examples 1 to 3. On the other hand, in the PET nonwoven fabrics (Comparative examples 1 to 3) to which no surface treatment agent have been treated, no improvement in the platelet recovering ability can be recognized. Also, from the SEM images of the blood filters of Example 3 and Comparative example 1 after filtration shown in FIGS. 1(a) and (b) and FIGS. 2(a) and (b), in Example 3, substantially no adhesion of the leukocytes, red blood cells and platelets to the PET nonwoven fabric could be admitted. This shows that the surface treatment agent (L) according to the present invention has a function of inhibiting adhesion of these blood corpuscles. In Comparative example 1, platelets were particularly and remarkably adhered to the PET nonwoven fabric, and adhesions of the leukocytes and red blood cells are observed to be progressing.

Test Example 2: Rabbit Platelet Recovering Performance of Nonwoven Fabric Made of PET to which Surface Treatment Agent (L) has been Fixed The respective PET nonwoven fabrics (Examples 6 and 7) subjected to the fixing method (Fixing methods No. 3 and No. 5) shown in Table 1 were punched to a size of φ 25 mm, and three sheets, five sheets or eight sheets thereof were each incorporated into the blood circuit to prepare samples for the blood filtering performance. As the blood, citrated fresh blood drawn out from a rabbit was used, and 7.5 ml thereof was filtered through each sample. Leukocyte concentrations, platelet concentrations and red blood cell concentrations before filtration and after filtration were each measured by an automatic Hematology Analyzer (manufactured by Sysmex Corporation, XT-2000i), and a leukocyte removing rate, a platelet recovering rate and a red blood cell recovering rate were obtained according to the following formulae. The results of Example 6 are shown in Table 3, and the results of Example 7 are shown in Table 4.

TABLE 3

(PET nonwoven fabric)

| Example 6 | Leukocyte removing rate (%) | Red blood cell recovering rate (%) | Platelet recovering rate (%) |
|---|---|---|---|
| Three sheets | 81 | 100 | 94 |
| Five sheets | 99 | 100 | 93 |
| Eight sheets | 100 | 100 | 78 |

TABLE 4

(PET nonwoven fabric)

| Example 7 | Leukocyte removing rate (%) | Red blood cell recovering rate (%) | Platelet recovering rate (%) |
|---|---|---|---|
| Three sheets | 90 | 101 | 94 |
| Five sheets | 97 | 100 | 91 |
| Eight sheets | 100 | 101 | 79 |

From Table 3 and Table 4, in the PET nonwoven fabrics (Examples 6 and 7) to which the surface treatment agent (L) has been fixed, no effect could be admitted to the platelet recovering ability even when five sheets have been overlapped.

Test Example 3: Rabbit Blood Filtering Performance of Surface Treatment Agent (L) Fixed to Nonwoven Fabric Made of Polypropylene (PP) and Nonwoven Fabric Made of Nylon The PP nonwoven fabric (Example 8: a basis weight of 40 g/m², a thickness of 0.5 mm, a fiber diameter of 1 to 2 μm, an air permeability of 12 cc/cm²/sec) and the Nylon nonwoven fabric (Example 9: a basis weight of 20 g/m², a thickness of 0.2 mm, a fiber diameter of 1 to 2 μm, an air permeability of 12 cc/cm²/sec) subjected to the fixing method (Fixing method No. 3) shown in Table 1 were punched to a size of φ 25 mm, and three sheets thereof were incorporated into the blood circuit to prepare samples for the blood filtering performance. As Comparative examples, an untreated (Fixing method No. 6) PP nonwoven fabric (Comparative example 4) and an untreated (Fixing method No. 6) Nylon nonwoven fabric (Comparative example 5) were used. As the blood, citrated fresh blood drawn out from a rabbit was used, and 7.5 ml thereof was filtered through each sample. Leukocyte concentrations, platelet concentrations and red blood cell concentrations before filtration and after filtration were each measured by an automatic Hematology Analyzer (manufactured by Sysmex Corporation, XT-2000i), and a leukocyte removing rate, a platelet recovering rate and a red blood cell recovering rate were obtained according to the following formulae. The results of the PP nonwoven fabrics of Example 8 and Comparative example 4 are shown in Table 5, and the results of the Nylon nonwoven fabrics of Example 9 and Comparative example 5 are shown in Table 6.

TABLE 5

(PET nonwoven fabric)

| | Fixing method | Leukocyte removing rate (%) | Red blood cell recovering rate (%) | Platelet recovering rate (%) |
|---|---|---|---|---|
| Example 8 | No. 3 | 47 | 101 | 44 |
| Comparative example 4 | No. 6 | 60 | 102 | 8 |

TABLE 6

(Nylon nonwoven fabric)

| | Fixing method | Leukocyte removing rate (%) | Red blood cell recovering rate (%) | Platelet recovering rate (%) |
|---|---|---|---|---|
| Example 9 | No. 3 | 90 | 101 | 91 |
| Comparative example 5 | No. 6 | 83 | 102 | 27 |

From Table 5 and Table 6, in particular, the Nylon nonwoven fabric to which the surface treatment agent (L) has been fixed was clearly improved in the platelet recovering ability while maintaining the leukocyte removing ability, as compared with those of Comparative example 5. Similarly, in the PP nonwoven fabric to which the surface treatment agent (L) has been fixed, the platelet recovering ability was confirmed to be improved.

Test Example 4: Human Blood Filtering Performance of Surface Treatment Agent (L) Fixed to Nonwoven Fabric Made of PET The PET nonwoven fabrics (Examples 10 and 11) subjected to the fixing method (Fixing methods No. 3 and 5) shown in Table 1 were punched to a size of φ 25 mm, and three sheets thereof were each incorporated into the blood circuit to prepare samples for the blood filtering performance. As Comparative example (Fixing method No. 6), an untreated PET nonwoven fabric (Comparative example 6) was used. As the blood, citrated human fresh blood drawn out from healthy volunteer was used, and 6.5 ml thereof was filtered through each sample. Leukocyte concentrations, platelet concentrations and red blood cell concentrations before filtration and after filtration were each measured by an automatic Hematology Analyzer (manufactured by Sysmex Corporation, XT-2000i), and a leukocyte removing rate, a platelet recovering rate and a red blood cell recovering rate were obtained according to the following formulae. The results are shown in Table 7.

TABLE 7

(PP nonwoven fabric)

| | Fixing method | Leukocyte removing rate (%) | Red blood cell recovering rate (%) | Platelet recovering rate (%) |
|---|---|---|---|---|
| Example 10 | No. 3 | 63 | 123 | 77 |
| Example 11 | No. 5 | 54 | 98 | 86 |
| Comparative example 6 | No. 6 | 63 | 94 | 19 |

From Table 7, the PET nonwoven fabrics (Examples 10 and 11) to which the surface treatment agent (L) has been fixed was clearly improved in the human platelet recovering ability while maintaining the human leukocyte removing ability, as compared with those of Comparative example 6.

Test Example 5: Rabbit Platelet Recovering Performance of Nonwoven Fabric Made of PET to which Surface Treatment Agent (M) has been Fixed The nonwoven fabrics made of PET (Comparative example 7 and 8: a basis weight of 38 g/m², a thickness of 0.2 mm, a fiber diameter of 1 to 2 an air permeability of 10 cc/cm²/sec, an average pore diameter of about 8 μm) to which the surface treatment agent (M) has been fixed were prepared by subjecting to the fixing method (Fixing methods No. 9 and 10) shown in Table 1. Thereafter, the nonwoven fabrics made of PET were punched to a size of φ 25 mm to prepare a filter. Three sheets thereof were incorporated into the blood circuit to prepare samples for the blood filtering performance. As Comparative example, an untreated (Fixing method No. 6) PET nonwoven fabric (Comparative example 9) was used. As the blood, citrated fresh blood drawn out from a rabbit was used, and 7.5 ml thereof was filtered through each sample. Leukocyte concentrations, platelet concentrations and red blood cell concentrations before filtration and after filtration were each measured by an automatic Hematology Analyzer (manufactured by Sysmex Corporation, XT-2000i), and a leukocyte removing rate, a platelet recovering rate and a red blood cell recovering rate were obtained according to the following formulae. The results are shown in Table 8.

TABLE 8

(PET nonwoven fabric)

| | Fixing method | Leukocyte removing rate (%) | Red blood cell recovering rate (%) | Platelet recovering rate (%) |
|---|---|---|---|---|
| Comparative example 7 | No. 9 | 61 | 101 | 78 |
| Comparative example 8 | No. 10 | 63 | 98 | 83 |
| Comparative example 9 | No. 6 | 53 | 97 | 64 |

Figure 3:
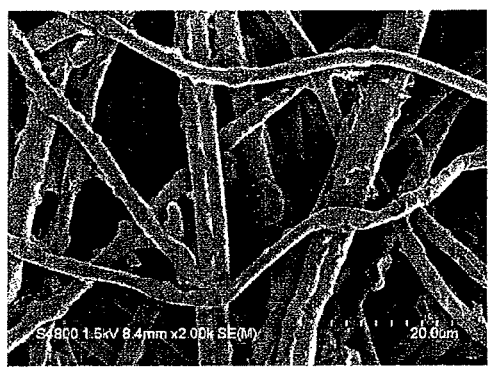
FIG. 3(a) is an SEM image (magnification: 2,000-fold) of the blood filter of Comparative example 7 after used in Test example 5.
FIG. 3(b) is an SEM image (magnification: 10,000-fold) in which a part of (a) is enlarged.
Figure 3:
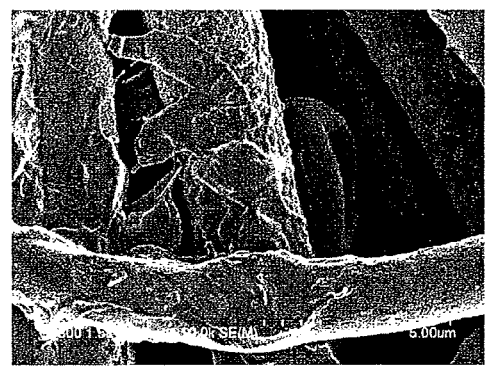

From Table 8, the PET nonwoven fabrics (Comparative examples 7 and 8) to which the surface treatment agent (M) has been fixed did not show clear platelet recovering ability as in the surface treatment material (L) shown in Table 2. Also, the SEM images of the blood filter of Comparative example 7 after filtration shown in FIGS. 3(a) and (b) showed particularly remarkable adhesion of the platelets, so that the surface treatment agent (M) was admitted to have a particularly low function of inhibiting adhesion to the platelets.

The invention claimed is:

1. A blood filter comprising
a porous element and
a coating that inhibits adhesion of biological substances, wherein the coating exists in at least a part of a surface of the porous element, and comprises a copolymer comprising (i) an ethylenically unsaturated monomer comprising the following formula (a) and (ii) an ethylenically unsaturated monomer comprising the following formula (b):

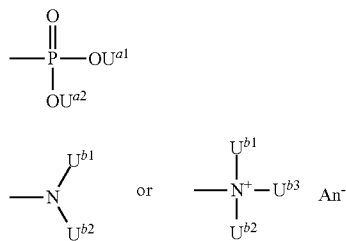

wherein $U^{a1}$, $U^{a2}$, $U^{b1}$, $U^{b2}$ and $U^{b3}$ each independently represent a hydrogen atom or a linear or branched alkyl group having 1 to 5 carbon atoms, and $An^-$ represents an anion selected from the group consisting of a halide ion, an inorganic acid ion, a hydroxide ion and an isothiocyanate ion.

2. The blood filter according to claim 1, wherein the ethylenically unsaturated monomers comprising the formulae (a) and (b) are derived from monomers of the following formulae (A) and (B), respectively:

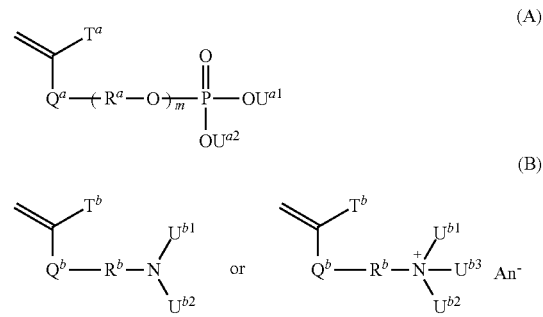

wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom, $An^-$ represents an anion selected from the group consisting of a halide ion, an inorganic acid ion, a hydroxide ion and an isothiocyanate ion, and m is an integer of 0 to 6.

3. The blood filter according to claim 2, wherein m is 1, and $R^a$ and $R^b$ each independently represent an ethylene group or a propylene group.

4. The blood filter according to claim 1, wherein the copolymer further contains a crosslinked structure derived from a monomer of the following formula (C) or (D):

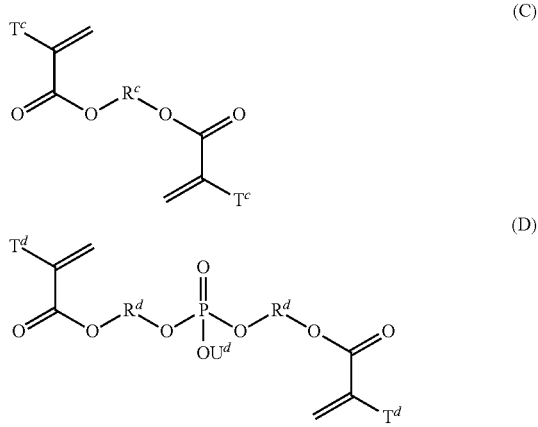

wherein $T^c$, $T^d$ and $U^d$ each independently represent a hydrogen atom or a linear or branched alkyl group having 1 to 5 carbon atoms, $R^c$ and $R^d$ each independently represent a linear or branched alkylene group having 1 to 10 carbon atoms which may be substituted by a halogen atom.

5. The blood filter according to claim 4, wherein $T^c$ and $T^d$ each independently represent a hydrogen atom or a methyl group, $U^d$ represents a hydrogen atom, and $R^c$ and $R^d$ each independently represent an ethylene group or a propylene group.

6. The blood filter according to claim 1, wherein the porous element is nonwoven fabric.

7. A method for manufacturing a blood filter of claim 1, which method comprises coating a copolymer comprising (i) an ethylenically unsaturated monomer comprising the following formula (a) and (ii) an ethylenically unsaturated monomer comprising the following formula (b):

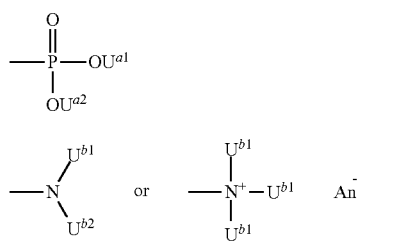

wherein $U^{a1}$, $U^{a2}$, $U^{b1}$, $U^{b2}$, and $U^{b3}$ each independently represent a hydrogen atom or a linear or branched alkyl group having 1 to 5 carbon atoms, and $An^-$ represents an anion selected from the group consisting of a halide ion, an inorganic acid ion, a hydroxide ion and an isothiocyanate ion onto at least a part of a surface of a porous element, and drying the coated porous element at −200° C. to 200° C.

8. The method according to claim 7, wherein the ethylenically unsaturated monomers comprising the formulae (a) and (b) are derived from monomers of the following formulae (A) and (B), respectively:

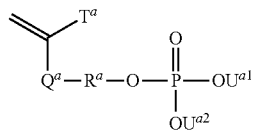

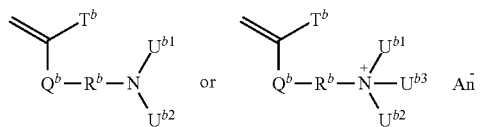

wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom, $An^-$ represents an anion selected from the group consisting of a halide ion, an inorganic acid ion, a hydroxide ion and an isothiocyanate ion, and m is an integer of 0 to 6.

9. The method according to claim 7, wherein the coating is carried out by using a varnish containing the copolymer.

10. The method according to claim 9, wherein the varnish containing a copolymer is previously adjusted a pH.

11. The method according to claim 7, wherein the method further comprises washing the coated porous element before and/or after the drying of the coated porous element.

12. The method according to claim 11, wherein the washing after the drying of the coated porous element is carried out by using at least one solvent selected from the group consisting of water and an aqueous solution containing an electrolyte.

* * * * *